United States Patent [19]

Bologna et al.

[11] Patent Number: 5,543,150
[45] Date of Patent: Aug. 6, 1996

[54] METHOD OF PROGESTERONE DELIVERY AND AFFECT THEREOF

[75] Inventors: William J. Bologna, New York; Howard L. Levine, Oceanside, both of N.Y.

[73] Assignee: Columbia Laboratories, Inc., Coconut Grove, Fla.

[21] Appl. No.: 122,371

[22] Filed: Sep. 15, 1993

[51] Int. Cl.$^6$ ............................. A61F 6/06; A61F 13/02; A61F 6/16; A61K 47/30
[52] U.S. Cl. ..................... 424/430; 424/431; 424/432; 424/433; 514/772.3; 514/841; 514/843; 514/967
[58] Field of Search ................................ 424/430, 431, 424/432, 433; 514/772.3, 841, 843, 967

[56] References Cited

U.S. PATENT DOCUMENTS 4,615,697 10/1986 Robinson ............................ 424/428

FOREIGN PATENT DOCUMENTS 0431719 6/1991 European Pat. Off. .
0002973 2/1993 WIPO .

OTHER PUBLICATIONS

Villaneuva, B., et. al., *Fertil. Steril.*, 35:433–437 (1981).
Arafat, E., et. al., "Sedative and Hypnotic Effects of Oral Admin. of Micronized Prog. May be Mediated through its Metabolites", Am. J. Obstet. Gynecol., 159:1203–1209 (1988).
Bigg, L. A., et., al., *J. Clin. Endocrinol. Metab.*, 45:1261–1272 (1977).
Maxon, W. S., *Clinical Obstet. Gynecol.*, 30;465–477 (1987).
Landgren, B., et. al., "Progesterone Releasing Vaginal Rings for Use in Post partum Contraception. II Pharmacokinetic Profiles in Women", *Contraception*, 45:343–349 (1992).
Nillius, S. & Johansson, E., "Plasma Levels of Progesterone after Vaginal, Rectal or Intramuscular Administration of Progesterone", Amer. J. Obstet. Gynec., 110:470–477 (1971).
Wilson, J. and Foster, D., "Disorders of the Ovary and Female Reproductive Tract", *Williams Textbook of Endocrinology* 214–229 (1985).
Norman, T. et. al., "Comparative Bioavailoability of Orally and Vaginally Administered Progesterone", Fert. and Sterility, 56:1034–1039 (1991).
Mishell, D., "The Pharmacology of Progestogens" *Menopause: Physiology and Pharmacology*, 321–331 (1987).
Cicinelli, E., et. al., "Comparative Study of Progesterone Plasma Levels after Nasal Spray and Intramuscular Administration of Natural Progesterone in Menopausal Women", *Gynecol. Obstet. Invest.*, 35:172–174 (1993).
Bardin, C. W., et al., "The Historic Review of the Clinical Use of Progesterone and Progestrin," Progetserone and Progestrins, 189–202 (1983).

*Primary Examiner*—Carlos Azpuru
*Attorney, Agent, or Firm*—Scott H. Blackman; Weil, Gotshal & Marges

[57] ABSTRACT

The present invention teaches that relatively low levels of serum progesterone, 1 to 6 ng/ml, may be used to prevent endometrial cancer. The vaginal delivery of progesterone using a cross-linked polycarboxylic polymer produces this low serum progesterone level while also providing the full secretory transformation of the endometrium, indicating the efficacy of the progesterone. Such low levels of serum progesterone will decrease the risk of breast cancer experienced by women undergoing hormone replacement therapy ("HRT") and minimize the potential of other undesirable progesterone associated side effects.

23 Claims, 3 Drawing Sheets

METHOD OF PROGESTERONE DELIVERY AND AFFECT THEREOF

BACKGROUND OF THE INVENTION

Progesterone is a naturally occurring steroid which is the main steroid secreted by women during their reproductive years. This steroid has been studied extensively and has been found to be a major precursor in the biosynthesis of most other steroids, particularly glucocortoids, androgens and estrogens. Progesterone also stimulates the growth of the uterus and a number of specific changes in the endometrium and myometrium. It is essential for the development of decidual tissue and the differentiation of luminal and glandular epithelial tissue. Progesterone also plays several roles in gestation, including breast enlargement, inhibition of uterine contractility, maintenance of gestation, immunological protection of the embryo, and inhibition of prostaglandin synthesis. Progesterone has been used pharmaceutically in the treatment of a number of clinical disorders such as luteal phase deficiency, dysfunctional uterine bleeding, endometriosis, endometrial carcinoma, benign breast disease, pre-eclampsia, and assisting in vitro fertilization, preventing early abortion and reducing the occurrence of endometrial hyperplasia in estrogen replacement therapy (ERT).

The most common progesteronal agents used are synthetic progesteronal agents which are accompanied by undesirable side effects such as depression and water retention. Additionally, many of the progestins derived from 19-nortestosterone reverse the positive effects of estrogen on lipoprotein (HDL) levels. On the other hand, natural progesterone does not cause water retention, is rarely associated with depression and has no adverse effects upon lipid levels.

Breast cancer, a disease affecting primarily menopausal women, has been linked with progesterone and thus, the risks associated therewith should be reduced as much as possible during hormonal replacement therapy (HRT), i.e., the delivery of both estrogen and progesterone. Proliferation of the terminal duct lobular unit, from which most breast cancers arise, is relatively low during the follicular phase (estrogen alone) of the menstrual cycle. It is then increased by a factor of two in the mid-to-late luteal phase (estrogen and progesterone). Thus, the combination of estrogen and progesterone appears to have a greater stimulatory effect on cell division than estrogen alone, as compared to progesterone being an anti-mitotic agent in the endometrium. These observations have led to the development of the "estrogen-augmented by progesterone" hypothesis of breast cancer etiology. This hypothesis posits that breast cancer risk is increased by estrogen alone but is increased further by simultaneous exposure of the breast epithelium to estrogen and progesterone. Data from a prospective study in Sweden have suggested that risk associated with combination HRT is higher than any found for ERT alone, as the breast mitotic rate data would suggest.

Another problem which has been linked with progesterone is central nervous system (CNS) depression. Too much progesterone can lead to fatigue and progesterone has even been used as a anesthetic in certain cases.

Them have been many difficulties in administering natural progesterone at the appropriate serum and tissue levels to patients. When given orally, progesterone is rapidly metabolized. See e.g., Adlecruz, H. and Martin, F. *J. Steroid Biochem.*, 13:231–244 (1980) and Maxson, W. S., and Hargrove, J. T., *Fertil. Steril.*, 44:622–626 (1985). Some studies have shown that significant tissue progesterone concentration may be achieved with a 200 mg dose whereby serum levels were noted for six hours, but there was a wide inter-patient variance. Maxson, W. S. and Hargrove, J. T., *Fertil. Steril.*, 44: 622–626 (1985); Whitehead, M. I., et al., *Br. Med. J.*, 180:825–827 (1980); Sitruk-Ware, R., et all., Contraception 36:373–402 (1987).

Rectal administration of progesterone has also been attempted with 25 mg and 100 mg doses of progesterone which achieved peak plasma progesterone levels at 4 to 8 hours after administration followed by a gradual decline, but the maintenance of a stable plasma level has been difficult with this route. Maxson, W. S. *Clinical Obstet. Gynecol.*, 30:465–477 (1987); Nillius, S. J. and Johansson, E. D. B. *Am. J. Obstet. Gynecol.*, 110:470–479 (1971). Sublingual administration resulted in rapid appearance of progesterone in the serum reaching peak values of up to 10 times basal levels, but returning to basal levels within twenty-four hours. Villanueva, B., et al., *Fertil. Steril,*, 35:433–437 (1981). Nasal administration, using 20 mg and 30 mg doses, achieved mean maximum concentrations of 2.1 and 4.1 ng/ml, respectively, at approximately 30 and 240 minutes, respectively.

Intramuscular administration of progesterone has been attempted with 100 mg doses which achieved 40 to 50 ng/ml serum concentrations in two to eight hours. Nillius, S. J. and Johansson, E. D. B., *Am, J, Obstet. Gynecol.*, 110:470–479 (1971). Such administration has shown that such injections need to be given every day or on alternate days to produce results. Whitehead, M., and Godfree, V. in Hormone Replacement Therapy, Churchill Livingston Edinburgh 1992, pp 91. Subdermal administration has also been assayed, with six 100 mg progesterone pellets being implanted in post-partum women. Croxatto, H. B., et al., *Acta Endocrinol*, 100: 630 (1982). Progesterone levels reached a peak of 4.4 ng/ml within the first week after insertion and reached a mean peak level of 1.9 ng/ml six months after implantation. Progesterone implants are not practical in cyclic therapy and moreover, physiological levels of progesterone are not achieved.

It has been demonstrated that topically applied radioactive progesterone can be absorbed through the skin. Mauvais-Jarvis, Progesterone., et al., *J. Clin. Endocrinol. Metab.*, 29:1580–1587 (1969). Labelled metabolites were recovered in the urine at 48 hours after topical administration. However, the absorption was only 10% of the applied dose. The high fat solubility of progesterone is responsible for the prolonged retention of this steroid and the extensive local metabolism reduces the systemic effect of the steroid. It has been shown that treatment with topical application of progesterone to the breast produces no changes in the endometrial histology or break-through bleeding. Sitruk-Ware, R., et al., *J. Clin. Endocrin. Metab.*, 44:771–774 (1977).

Progesterone has also been administered vaginally to postmenopausal women receiving ERT. Villanueva, B., et al., *Fertil. Steril.*, 35:433–437 (1981). 50 mg/ml of progesterone in a suspension containing carboxymethyl cellulose and methylcellulose which was inserted into the vagina was characterized by a rapid absorption of the progesterone across the vaginal mucosa. There was an immediate appearance of the hormone in the peripheral circulation resulting in a 10-fold increase over the baseline serum levels (0.34 ng/ml) after 15 minutes. The peak levels were obtained 1 or 2 hours after administration and represented a 30–40-fold increase over baseline levels (12.25 ng/ml). The serum levels remained at this level over the next seven hours, declining over the next ten hours to 3.68 ng/ml. Villanueva, B., et at., Fertil. Steril., 35:433–437 (1981). These studies suggested that the absorption of progesterone was enhanced in women also undergoing ERT.

The vaginal administration of progesterone is complicated by a variability within and among patients. Side effects have included vaginal irritation and discharge, monilial vaginitis, pruritus and occasional delayed onset of menses. Maxson, W. S. Clinical Obstet. Gynecol., 30:465–477 (1987). However, no long term-side effects have been reported.

SUMMARY OF THE INVENTION

The present invention comprises the use of a drug delivery formulation based upon a cross-linked polycarboxylic acid polymer to deliver progesterone locally in the vagina. This method of delivery has produced serum levels of progesterone between 1 ng/ml and 6 ng/ml while still producing full endometrial secretory transformation. In this way a low circulatory level of progesterone decreases the risk of side effects while protecting against endometrial cancer.

DETAILED DESCRIPTION OF THE INVENTION

Figure 1:
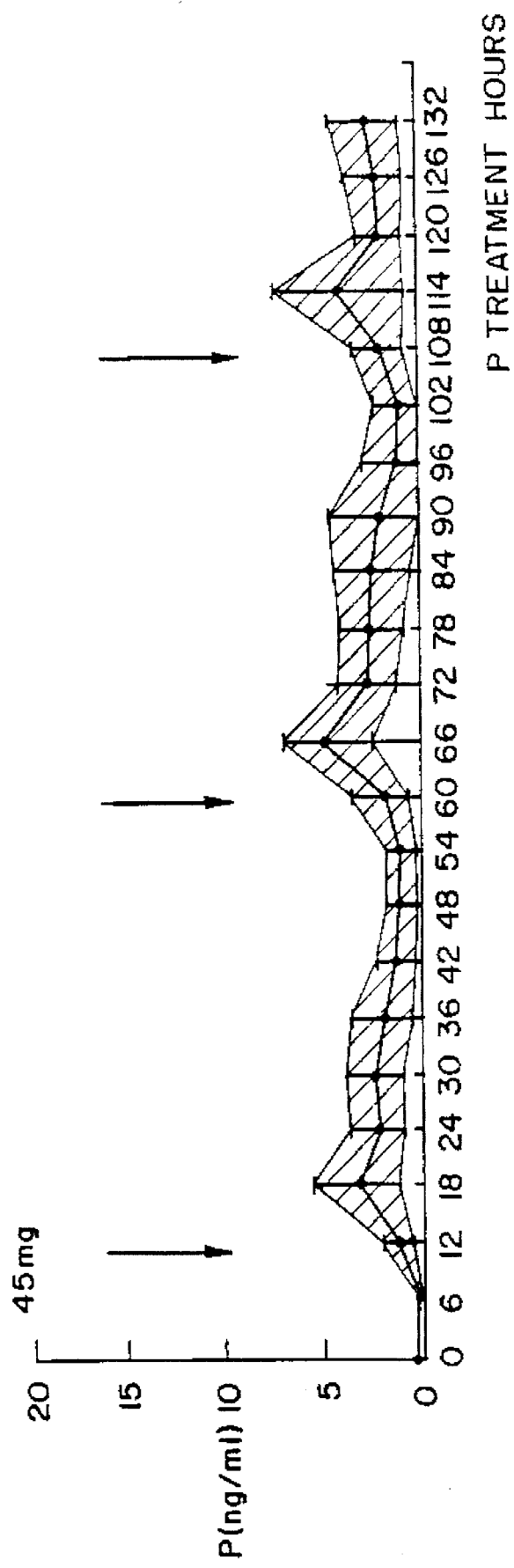
FIG. 1 illustrates the effect of a 45 mg dose of progesterone administered every other day vaginally as per the present invention on the serum progesterone levels of women who had experienced ovarian failure.

The present invention is related to a method of vaginally administering progesterone to women in an improved fashion. The progesterone which is used to prevent endometrial cancer should be present in the systemic circulation and in the breast at the lowest concentrations and for the minimum number of days each cycle required to produce the antiproliferative effect in the endometrium to keep at a minimum the risk of breast cancer presented by progesterone. Moreover, low serum levels of progesterone are preferred because of CNS depression and other possible side effects. By using a slow release bioadhesive polymer with a relatively low amount of progesterone to release progesterone in the vagina a surprising result has been discovered, that a fully secretory endometrium occurs at very low serum levels of progesterone, at levels which minimize the risk of breast cancer and other progesterone associated side effects. Such a method thereby provides for the targeted delivery of progesterone.

The secretory-phase transformation of the endometrium after progesterone administration is taken as an indicator that the therapeutic effects of the progesterone have been achieved in the endometrium. Using the present invention one may achieve this secretory transformation in the endometrium with vaginally administered progesterone while maintaining low circulating serum concentrations, at about 1 ng/ml to about 6 ng/ml, and preferably about 1 to 4 ng/ml and more preferably, about 1 to 2 ng/ml. The prior art, including vaginal suppositories, required circulating progesterone levels that were much greater, about 10 to 12 ng/ml, to affect the same changes. The "normal" physiological luteal phase serum progesterone concentrations must attain serum levels of at least 7 ng/ml to produce secretory transformation of endometrium, which had been the physiological concentration that had been thought necessary to produce a secretory transformation in the endometrium.

That the results of endometrial biopsies after use of the present invention indicated secretory phase transformation exceeded the expectation drawn from such progesterone levels speak for a uterine selectivity of the transvaginal route of administration. By this, it is postulated that part of the progesterone administered transvaginally transits through the uterus prior to reaching the general circulation. The exact mechanism of this "first uterine pass" effect is not yet fully understood. Three hypothesis can be put forth for explaining the data supporting the first uterine pass effect: (1) transvaginally administered progesterone may transit to the uterus through the local circulatory system, (2) there may be direct diffusion of progesterone into the uterus, or (3) progesterone may reach the uterus through the lymphatics. In support of this later hypothesis is the established knowledge that vaginal cancer from the upper one-third of the uterus tends to disseminate following the uterine lymphatic tracks. According to the second hypothesis, progesterone could diffuse passively between cells and reach the uterus by proximity. Given the results produced by using the present invention, one may target the endometrium and thereby minimize waste of progesterone, circulatory levels of progesterone and concomitant side effects.

The present invention approaches the ideal of minimizing cancer risks associated with HRT. The concentration of progesterone introduced to the body by the present invention is insufficient to increase the mitotic rate in the terminal duct lobular unit while providing a positive affect on the endometrium.

Another advantage of the present invention is that when 10 mg to 200 mg doses of progesterone are dispensed for the prevention of endometrial cancer in menopausal women receiving HRT, the coronary vasodilating effect of estrogen is not reversed.

Additionally, the present invention indicates the lack of utility of combination estrogen/progesterone patches and the use of combination oral contraceptives for HRT. These regimens would expose the breast to a daily stimulation by a combination of high levels of estrogen and progesterone.

To achieve the desired serum levels of 1–6 ng/ml of progesterone for continuous periods of about forty-eight hours while achieving endometrial secretory transformation 10 m 200 mg of progesterone should be delivered to the vagina in a drug delivery system according to the present invention every other day for twelve days (six doses), which will release to the vagina on daily basis only 10–12 weight percent of the progesterone actually inserted. The amount of progesterone in the drug delivery system delivered to the vagina necessary to achieve a desired serum progesterone level will vary depending upon the physiological conditions of the patient and the release rate of the polymer used in the drug delivery system. Moreover, if daily or more frequent dosages of progesterone are desired, the amount of progesterone to be delivered in each dosage may be decreased.

The serum progesterone levels are maintained within a relatively narrow range, i.e., 1–6 ng/ml, by the present invention and do not fluctuate after each dose as of those previously known. Moreover, while the endometrial levels of progesterone are not readily calculable, it appears that there is a steady state effect in the endometrium because the secretory phase transformation lasts for the period of treatment.

45 mg of progesterone administered vaginally every other day with the present invention produces a barely measurable serum concentration of 1 to 3 ng/ml while producing a secretory transformation. Clinical research has shown that this level of progesterone administration over twelve days will inhibit the proliferative effects of estrogen in the endometrium. A 90 or 180 mg dose of progesterone delivered every other day with the present invention produces a serum concentration of approximately 4–6 ng/ml, again while providing the anti-mitotic and secretory transformative effect in the endometrium. These larger doses may be needed in women undergoing in vitro fertilization (IVF) procedures. In IVF, the endometrium must become receptive to the developing egg solely based on exogenous hormones, which can be accomplished with estradiol ($E_2$) and progesterone replacement regimes. Such low serum progesterone level would assist in avoiding the side effects of the progesterone, e.g., CNS depression and the risk of breast cancer, during IVF.

The drug delivery system of the present invention is described in U.S. Pat. No. 4,615,697 to Robinson (hereinafter "the '697 patent"), which is incorporated herein. Said bioadhesive polymeric system has the advantage of being held in the vagina for relatively long periods of time, i.e., 48 to 72 hours, whereas most drug delivery systems are sloughed off the vaginal walls in less than four hours. The polymer holds the progesterone and slowly releases it over time. The drug delivery system allows for direct contact with the vaginal epithelium which allows direct delivery to the target organ, as discussed above. The delivery system surprisingly delivers enough progesterone to the endometrium while maintaining such low circulatory levels, thus providing a targeted method of progesterone delivery.

The polymers of the '697 patent are cross-linked polymers wherein at least eighty percent of the monomers of which the polymer is comprised contain at least one carboxyl functionality. A preferred polymer for use herein is Polycarbophil, U.S.P. which is commercially available from B. F. Goodrich Specialty Polymers of Cleveland, OH under the trade name NOVEON®-AA1. Said polymers should not be used in their salt form because this would decrease their bioadhesive capability. The cross-linking agent should be present at about 0.1 to 6.0 weight percent of the polymer, with about 1.0 to 2.0 weight percent being preferred. Suitable cross-linking agents include divinylbenzene, N,N-diallylacrylamide, 3,4-dihydroxy-1,5 hexadiene, 2,5-dimethyl-1,5-hexadiene and similar agents. Additionally, the adjuvants taught in the '697 patent should be included with the cross-linked polymer for maximum efficacy of the drug delivery system and for the comfort of the patient. Such adjuvants include lubricants, plasticizing agents, binders, vehicles, coloring agents, taste and/or smell controlling agents, viscosity controlling agents and similar agents.

The polymers described in the '697 patent may be adjusted to control the release rate of the progesterone, e.g., by varying the amount of cross-linking agent. Generally, the release rate is first order on the amount of drug in the polymer, so the release rate should be adjusted to deliver an appropriate amount of progesterone with the knowledge that the polymer stays in place for about 48 hours. It has been estimated that approximately 10%–12% of the amount of the progesterone in the drug delivery system is actually released from the polymer therein during a twenty-four hour period.

The drug delivery system with the drug therein may be delivered to the vagina in a variety of fashions as are known in the art, e.g., plunger, douche, and manually. A preferred method of delivery is using those devices described in U.S. design patent applications Ser. Nos. 07/863,879 and 07/862,282. These devices are oblong hollow containers, with one end capable being opened and the other end containing most of the drug to be delivered and capable of being squeezed. Such devices allow for pre-measurement of the amounts of polymer and drug to be delivered in a sealed container which may be used relatively easily by women. Said containers also maintain the drug and polymer in a sterile environment until use. Upon use the containers are opened and the open end is inserted into the vagina, while the other end is squeezed to expel the contents of the container into the vagina.

EXAMPLE

Eighteen young women deprived of ovarian function prematurely and future candidates for in vitro fertilization with egg donation volunteered for a study. The excellent pregnancy rates that have been universally reported with egg donation has led to the use of estradiol and progesterone replacement cycles as study model for analyzing the hormonal control of endometrial receptivity. In previous studies it has been shown that marked decreases or increases in luteal estradiol levels fail to affect endometrial morphology at the time of embryo implantation (day 20) or in the late luteal phase (day 24), thus progesterone levels are probably the important hormone to vary. In all the patients of the study it was documented that ovarian failure was complete by a baseline ultrasound and hormonal profile (low $E_2$ (estradiol) and high follicle stimulating hormone (FSH levels)). After having been extensively informed about the planned study, the patients were enrolled and received transdermal $E_2$ at doses varying from 0.1 to 0.4 mg, using one or several transdermal system (Estraderm™ TTS 100, Ciba Pharmeceuticals, Paris, France) delivering 0.1 mg of $E_2$ per day, each. On day 15 after having received 14 days of $E_2$ priming, the patients were admitted in a clinical research center. Starting on the morning of day 15, patients were randomized to receive one of the three progesterone doses. Progesterone was administered vaginally using a time release system, made according to present invention, which was comprised of 12.9 weight percent glycerin, 4.2 weight percent mineral oil, 1 weight percent hydrogenated palm oil glyceride, 0.08 weight percent sorbic acid, 0.18 weight percent methylparaben, 1 weight percent CARBOPOL 934P (available from B. F. Goodrich), 2 weight percent polycarbophil, either 4 or 8 weight percent progesterone and the remaining part water. 45, 90 and 180 mg doses of progesterone were administered, with, for the 45 mg doses, the 4 weight percent progesterone composition being used and for the 90 mg and 180 mg doses, the 8 weight percent composition being used. For example, to deliver 45 mg doses of progesterone 1.125 gms of the 4 weight percent progesterone composition was used. The 3 doses of progesterone were randomly and blindly assigned to 3 groups of 6 patients each. These doses were administered at 11 o'clock on day 15 and repeated every other day until day 25 (6 applications in all). During the 6 day hospital stay, the patients had serial blood samplings every 6 hours for hormonal measurements ($E_2$, estrone, LH (luteinizing hormone), FSH and progesterone). They also had daily transvaginal ultrasound using a high resolution probe (ATL-HDI, 5–9 MHZ). A 15 minute sequence of endometrial ultrasound scan was taped on the S-VHS system for later off-fine image analysis using an appropriate computerized system.

The 18 patients participating in the study had endometrial biopsies on day 24 (6 patients per progesterone dose group). Aside from serial blood samplings obtained during the 6 day spent in the clinic, all the patients also had blood samples obtained twice a week while receiving treatment.

Figure 2:
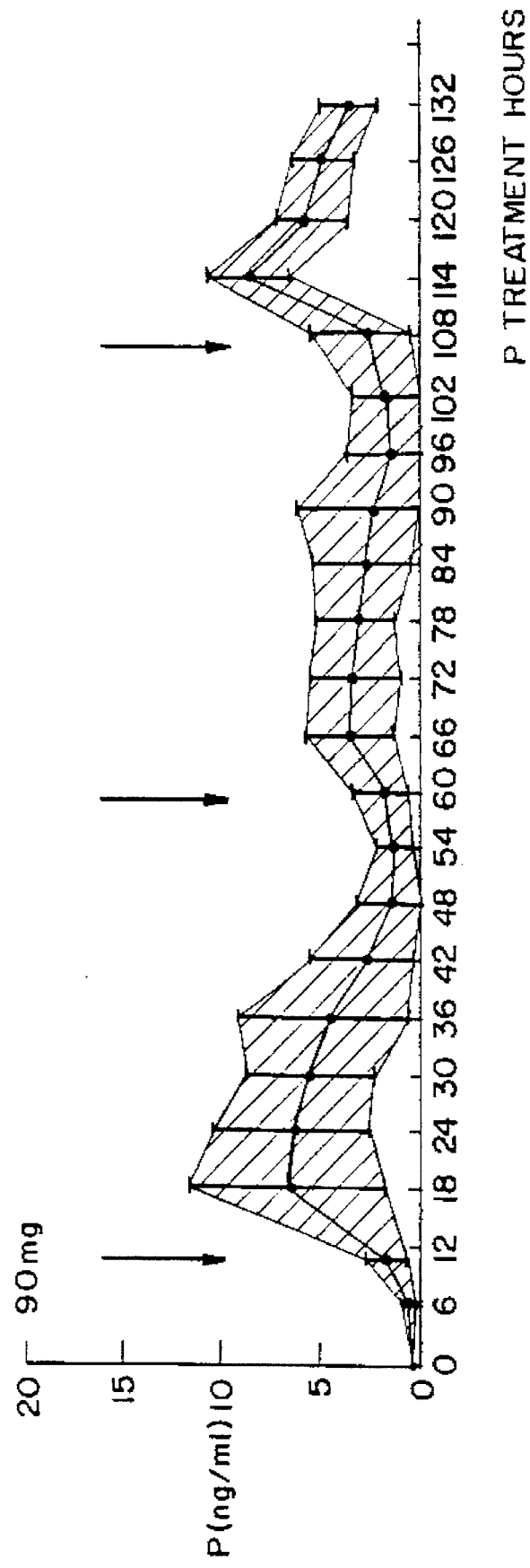
FIG. 2 illustrates the effect of a 90 mg dose of progesterone administered every other day vaginally as per the present invention on the serum progesterone levels of women who had experienced ovarian failure.
Figure 3:
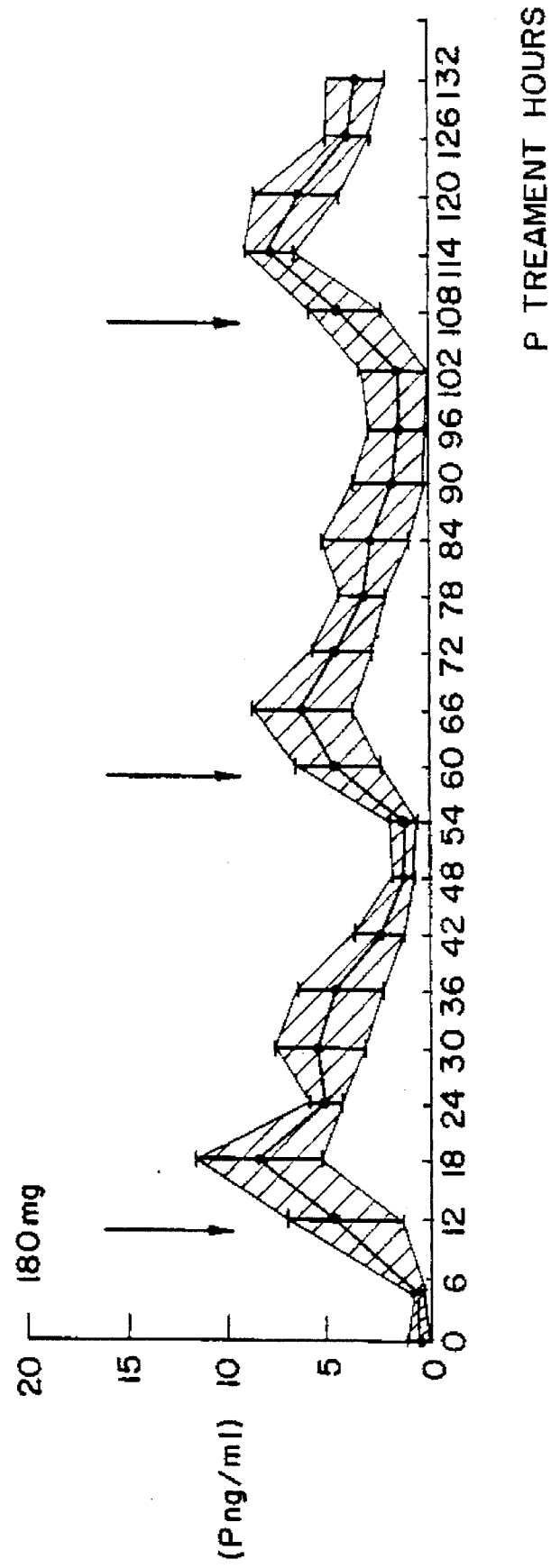
FIG. 3 illustrates the effect of a 180 mg dose of progesterone administered every other day vaginally as per the present invention on the serum progesterone levels of women who had experienced ovarian failure.

Endometrial biopsies obtained from the 18 patients on day 24 showed full secretory changes of the endometrial stroma, except in two patients who displayed signs usually seen at the time of menses (menstrual endometrium). In these two patients, some degree of secretory changes were noticed in the endometrial stroma. These 2 patients were treated with 180 and 90 mg doses, respectively. The secretory changes in the endometrial stroma observed in the other 16 patients showed complete predecidualization. Echographic data confirmed the appropriateness of the $E_2$ priming by displaying individual values of endometrial thickness being comprised between 5 and 12 mm. Plasma progesterone levels observed during the first 6 days of progesterone therapy are illustrated in FIGS. 1–3 with each figure representing the 45, 90, 180 mg dosed women, respectively. Resulting median serum progesterone levels in ng/ml were plotted, with the shaded area representing a 95% confidence interval limit, versus the days of progesterone therapy. As can be seen, the progesterone levels achieved by the two larger doses (90 and 180 mg) appear similar, being between 2 to 8 ng/ml. On the contrary, plasma progesterone levels achieved with every second day applications of the 45 mg dose are lower, being between 1 to 3 ng/ml. From these data, it is remarkable that full secretory transformation has been observed in all the patients receiving the 45 mg dose. Indeed, from the data existing in the literature, as well as from the experience of the researchers conducting the experiment, it would have been anticipated that such lower plasma progesterone levels would have resulted in markedly abnormal day 24 endometrial biopsies.

We claim:

1. A method of delivering progesterone to women comprising delivery of progesterone via a drug delivery system inserted into the vagina in an amount sufficient to cause secretory transformation of the endometrium while maintaining serum levels of progesterone below 6.0 ng/ml for a continuous period of at least forty-eight hours.

2. A method according to claim 1 wherein 10–200 milligrams of progesterone are inserted into the vagina.

3. A method according to claim 1 wherein the serum level is 1 to 4 ng/ml of progesterone.

4. A method according to claim 1 wherein adjuvants are also inserted into the vagina.

5. A method according to claim 1 wherein the vagina has been primed with estradiol.

6. A method according to any one of claims 1–5 wherein the drug delivery system comprises a cross-linked polycarboxylic polymer and progesterone.

7. A method according to claim 6 wherein the polymer is polycarbophil.

8. A method of targeting the delivery of progesterone to the endometrium comprising inserting into the vagina a drug delivery system comprising a cross-linked carboxylic polymer and progesterone wherein 10–200 milligrams of progesterone are inserted into the vagina.

9. A method according to claim 8 wherein the resulting serum level of progesterone is 1 to 4 ng/ml of progesterone.

10. A method according to claim 8 wherein the polymer is polycarbophil.

11. A method of targeting the delivery of progesterone to the endometrium comprising inserting into the vagina a drug delivery system comprising a cross-linked carboxylic polymer and progesterone wherein the drug delivery system additionally comprises at least one adjuvant.

12. A method of causing secretory transformation in the endometrium while maintaining serum levels of progesterone between about 1 to less than about 5 ng/ml.

13. A method of causing secretory transformation in the endometrium while maintaining serum levels of progesterone between about 1 to 6 ng/ml, wherein the progesterone level is achieved by inserting into the vagina a drug delivery system comprising a cross-linked polycarboxylic polymer and progesterone.

14. A method according to claim 13 wherein 10–200 milligrams of progesterone are inserted into the vagina.

15. A method according to claim 13 wherein the serum level is 1 to 4 ng/ml of progesterone.

16. A method according to claim 13 wherein the polymer is polycarbophil.

17. A method according to claim 13 wherein the drug delivery system additionally comprises at least one adjuvant.

18. A method according to claim 13 wherein the vagina has been primed with estradiol.

19. A method according to claim 13 wherein the polymer is cross-linked with 0.1 to 6.0 weight percent of the polymer of a cross-linking agent.

20. A method according to claim 12 wherein the progesterone level is maintained between about 1 to 4 ng/ml.

21. A method according to claim 20 wherein the progesterone level is maintained between about 1 to 2 ng/ml.

22. A method according to any one of claims 12, 20 and 21 wherein the progesterone is delivered via a drug delivery device inserted into the vagina.

23. A method according to claim 6 wherein the polymer is cross-linked with about 0.1 to 6.0 weight percent of the polymer of a cross-linking agent.

* * * * *